(12) United States Patent
Li et al.

(10) Patent No.: US 7,803,186 B1
(45) Date of Patent: Sep. 28, 2010

(54) PROSTHETIC HEART VALVES WITH FLEXIBLE LEAFLETS AND LEAFLET EDGE CLAMPING

(75) Inventors: XueMei Li, Shoreview, MN (US); Yi-Ren Woo, Woodbury, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 81 days.

(21) Appl. No.: 11/906,181

(22) Filed: Sep. 28, 2007

(51) Int. Cl.
*A61F 2/06* (2006.01)

(52) U.S. Cl. ............ 623/2.19; 623/2.1; 623/2.12; 623/2.17; 623/2.18

(58) Field of Classification Search ........ 623/2.12–2.15, 623/2.17–2.19
See application file for complete search history.

(56) References Cited

U.S. PATENT DOCUMENTS

| | | | |
|---|---|---|---|
| 4,506,394 A | 3/1985 | Bedard | |
| 5,037,434 A | 8/1991 | Lane | |
| 5,147,391 A | 9/1992 | Lane | |
| 5,910,170 A * | 6/1999 | Reimink et al. | ............ 623/2.38 |
| 6,102,944 A | 8/2000 | Huynh et al. | |
| 6,338,740 B1 | 1/2002 | Carpentier | |
| 6,461,382 B1 | 10/2002 | Cao | |
| 6,530,952 B2 | 3/2003 | Vesely | |
| 6,558,418 B2 | 5/2003 | Carpentier et al. | |
| 6,719,789 B2 | 4/2004 | Cox | |
| 7,201,771 B2 | 4/2007 | Lane | |
| 2002/0173842 A1 * | 11/2002 | Buchanan | ............... 623/2.14 |
| 2004/0078074 A1 | 4/2004 | Anderson et al. | |
| 2004/0193261 A1 | 9/2004 | Berreklouw | |
| 2006/0235508 A1 | 10/2006 | Lane et al. | |

* cited by examiner

*Primary Examiner*—David Isabella
*Assistant Examiner*—Yashita Sharma
(74) *Attorney, Agent, or Firm*—Lerner, David, Littenberg, Krumholz & Mentlik, LLP

(57) ABSTRACT

A prosthetic heart valve includes an annular stent structure having a plurality of annularly spaced stent post regions, a plurality of leaflets that extend radially inward from the stent structure and that include radially outer portions that lie against a radially outer surface of the stent structure, and a clamping structure that is radially outside the other components and that clamps the radially outer portions of the leaflets against the radially outer surface of the stent structures to secure the leaflets to the stent structure. The above-described structural arrangement applies to the stent post regions as well as to other portions of the stent structure.

18 Claims, 4 Drawing Sheets

PROSTHETIC HEART VALVES WITH FLEXIBLE LEAFLETS AND LEAFLET EDGE CLAMPING

BACKGROUND OF THE INVENTION

This invention relates to prosthetic heart valves with flexible leaflets that are supported by a stent structure, and more particularly to techniques for securing the leaflets to the stent structure.

Prosthetic heart valves with flexible leaflets supported by a stent structure are well known. A typical technique for attaching the leaflets to the stent structure includes suturing the leaflets to the stent structure. Such suturing is labor-intensive, and the quality of the resulting prosthesis can be dependent on the skill of the person doing the suturing. For example, the forces applied by the suture(s) may not be well-controlled, which can affect the local geometry of the leaflet at the location of the suturing attachment. This can adversely affect the service life of the prosthesis.

SUMMARY OF THE INVENTION

In accordance with certain possible aspects of the present invention, a prosthetic heart valve may include a stent structure that extends annularly around the valve and that includes a plurality of stent post structures that are spaced from one another around the valve. The valve further includes a plurality of leaflets that extend radially inward from the stent structure. Each leaflet has a radially outer portion that lies against a radially outer surface of the stent structure including the stent post structures. The valve still further includes a clamping structure that fits over the radially outer portions of the leaflets and that clamps the radially outer portions of the leaflets to the stent structure including the stent post structures.

In accordance with certain other possible aspects of the invention, a prosthetic heart valve includes a stent member that extends annularly around the valve and that undulates substantially parallel to a longitudinal axis that passes through the valve and about which the valve is annular. Undulations of the stent member cause the stent member to form a plurality of stent post regions that extend from a remainder of the stent member in a blood-outflow direction when the valve is in use in a patient. The stent post regions are spaced from one another in a direction that is annular of the valve. The valve further includes a plurality of leaflets that extend radially inward from the stent member. Each leaflet has a radially outer portion that lies against a radially outer surface of the stent member including the stent post regions. The valve still further includes a clamping structure that is disposed radially outside of a radially outer surface of the radially outer portions of the leaflets and that clamps the radially outer portions of the leaflets radially inwardly against the radially outer surface of the stent member including the stent post regions.

Further features of the invention, its nature and various advantages, will be more apparent from the accompanying drawings and the following detailed description.

DETAILED DESCRIPTION

Figure 1:
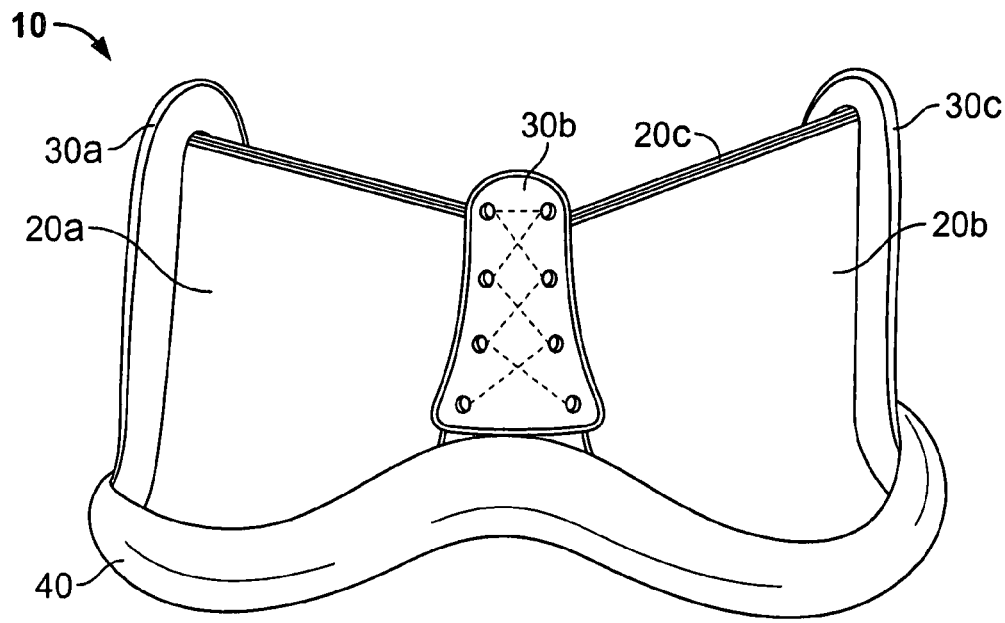
FIG. 1 is a simplified perspective or isometric view of an illustrative embodiment of a finished or nearly finished prosthetic heart valve in accordance with the invention.

As mentioned briefly above, FIG. 1 shows an illustrative embodiment of a finished or nearly finished prosthetic heart valve 10 in accordance with the invention. The components of valve 10 that are visible in FIG. 1 include three flexible leaflets 20a, 20b, and 20c; three stent post covers 30a, 30b, and 30c; and sewing cuff 40. The upper free edges of leaflets 30 can come together in a Y-shaped pattern (when viewed from above) to close the valve as shown in FIG. 1. The valve closes in this fashion when the pressure of the blood above the valve (as viewed in FIG. 1) is greater than the pressure of the blood below the valve. The free edges of the leaflets move apart to open the valve and to let blood flow through valve in the upward direction as view in FIG. 1 when the pressure of the blood below the valve is greater than the pressure above the valve.

FIGS. 2-5 show various components that are included in valve 10.

Figure 2:
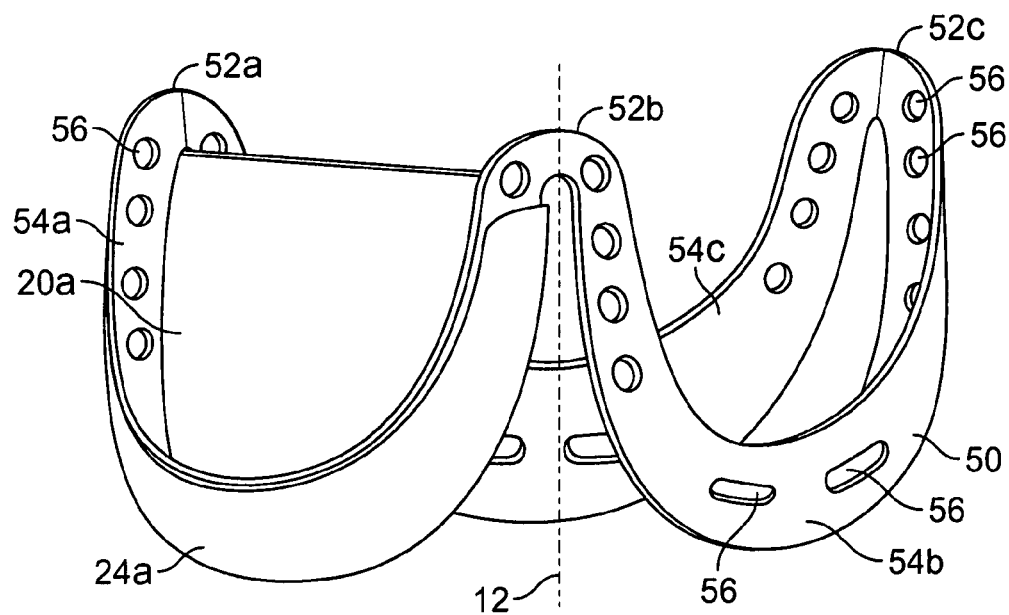
FIG. 2 is a view of the same general kind as FIG. 1, but showing the valve only partly assembled.

The components that are visible in FIG. 2 include stent 50 and a representative one of leaflets 20 (in particular, leaflet 20a) in position on the stent. FIG. 5 provides another view of representative leaflet 20a by itself. Stent 50 is typically a metal or plastic member that is annular about a central longitudinal axis of the valve (i.e., an approximately vertical axis 12 as viewed in FIG. 2 or FIG. 4). Stent 50 undulates up and down as one proceeds annularly around the stent. This undulation produces three "high" portions 52a, 52b, and 52c that are equally spaced from one another around the stent. Each of these high portions corresponds to a respective one of three commissure regions of the valve. A commissure region may also be known as a commissure post or stent post, and the upper end of such a commissure post may be known as a commissure tip. Between each annularly adjacent pair of commissure tips, stent 50 curves down and away from either of the commissure tips in that pair, and then up toward the other commissure tip in that pair. Such portions of stent 50 may be referred to as in inter-commissure portions of the stent, and they are assigned reference numbers 54a-c in the FIGS.

As can perhaps best be seen in FIG. 5, each of leaflets 20 has a main "belly" portion 22, and a roll-back wing portion 24. The belly portion 22 of each leaflet is the actual operating portion of the leaflet when in a finished and implanted valve. The roll-back portion 24 of each leaflet is the portion that is used to secure the leaflet to the stent 50 of the valve. Each inter-commissure portion 54 of stent 50 fits into the pocket 26 that is formed between the belly 22 and the roll-back portion 24 of a respective one of leaflets 20. FIG. 2 shows this for representative leaflet 20a. When this is done, the belly portion 22 of each leaflet includes enough material between the commissure posts 52 of stent 50 so that the upper free edges of the three leaflet belly portions can come together in the interior of the valve to close the valve as shown in FIG. 1.

After the three leaflets 20 have been placed on stent 50 as described above, cuff support 42 (FIG. 4) is placed around the lower portion of assembly 20/50, and a respective one of post covers 30 is placed on each of the three portions of assembly 20/50 that project above cuff support 42. Cuff support 42 may be a plastic ring that undulates in the same general way as stent 50 as one proceeds around the valve. The undulations of cuff support 42 are, however, much smaller than the undulations of stent 50, so that the three relatively high portions of support 42 do not extend up nearly as far as the tips of stent posts 52. Post covers 30 cover the radially outer surface of assembly 20/50 that is thus left exposed after cuff support 42 has been added around the outside of the lower portion of assembly 20/50.

A silicone cuff 44 may be on the outside of cuff support 42 when support 42 is added to assembly 20/50, or cuff 44 may be added later. Silicone cuff 44 is (or is at least an important component of) sewing cuff 40 in the finished valve.

The inside diameter of cuff support 42 is preferably larger than the outer diameter of stent 50.

However, this difference in diameters is preferably small enough so that roll-back wing material 24 of leaflets 20 that is disposed between members 42 and 50 is at least lightly gripped or clamped between those members. Sutures can be passed through aligned apertures 46 and 56 in members 42 and 50 to secure those members together. These sutures may also pass through roll-back wing material 24 between members 42 and 50, and if so, such sutures will also help to secure leaflets 20 to stent 50. However, the above-mentioned gripping or clamping of roll-back wing material 24 between members 42 and 50 remains an important (preferably the primary) mechanism for securing leaflets 20 to stent 50. This is advantageous because this clamping or gripping extends over a much larger area of leaflet material than a suture can. The leaflet retention force or pressure can therefore be distributed much more widely and uniformly by the gripping or clamping effected by members 42 and 50. In addition, such leaflet retention force or pressure due to gripping or clamping between members 42 and 50 can be more predictable and uniform from valve to valve because it is a function of machine-made part sizing rather than individual operator performance (e.g., as in the case of exclusive reliance on suturing to secure leaflets to a stent).

Each of post covers 30 can be a plastic member that is flat, relatively flat, or concave on the inside (toward the center of the valve) to match or mate with the radially outer convexity of the portion of assembly 20/50 that the post cover will be applied over. Each post cover 30 has a plurality of apertures 36 that align with other apertures 56 in stent 50 when the post cover is placed against assembly 20/50. Stitching (e.g., of suture material) can be passed through these aligned apertures 36 and 56 to hold each post cover to the assembly 20/50. Some or all of this stitching may pass through roll-back wing material 24 that is thus trapped between stent 50 and each post cover 30. In that event, this stitching will contribute to securing leaflets 20 to stent 50.

Whether or not there is such a stitching contribution, a more important contribution is made by the clamping of roll-back wing material 24 between members 30 and 50. As in the case of roll-back wing clamping between members 42 and 50, roll-back wing clamping between members 30 and 50 can distribute leaflet retention force or pressure more widely and more uniformly across more of material 24 than could be effected by stitching through material 24 alone and without the presence of members 30 to act as larger force- or pressure-distributing clamps.

From the foregoing it will be seen that the primary means by which leaflets 20 are secured to stent 50 are the presence of the roll-back wings 24 of leaflets 20 between members 42 and 50 in the lower portion of the valve and between members 30 and 50 in the upper portion of the valve. Folding roll-back wings 24 around the edge of stent 50 already transfers some force from leaflets 20 to stent 50. Moreover, this force transfer is done in a highly uniform manner that is distributed lengthwise along the length of the stent edge. Then further force transfer from the leaflets to the stent is performed by the clamping effect of members 30 and 42 clamping the roll-back wings against the outer surface of the stent. Again, this further force transfer tends to be distributed over relatively large areas of the roll-back wing material because the clamping between members 30 and 42, on the one hand, and stent 50, on the other hand, tends to engage such relatively large areas of the roll-back wings. The load, therefore, is not concentrated at a few individual points, as would be the case if the sole or primary reliance was on stitching through the leaflet material.

Another possible way to characterize the clamping structures of this invention (and to distinguish them from prior art suturing) is by saying that such a clamping structure extends longitudinally along the portion of a valve leaflet where that leaflet meets the supporting stent structure. The stent structure also includes a member that extends longitudinally along that portion of the leaflet. Thus a longitudinal portion of the leaflet (which is typically adjacent and approximately parallel to the edge of the leaflet that is not in the flow of blood through the implanted valve) is clamped along its length between two other longitudinal structures. These two other longitudinal structures are (1) the above-mentioned longitudinal member of the stent structure, and (2) the above-mentioned clamping structure. The leaflet clamping of this invention is therefore longitudinal in extent, and it is preferably continuous or substantially continuous along the length of that longitudinality.

It should be especially noted that where the free edges of leaflets 20 attach to the commissure posts 52 of stent 50 there can be relatively high force tending to pull the leaflets away from the stent posts. This can make post covers 30 especially important components of valves in accordance with this invention. This is so because, as has been mentioned, the provision of roll-back wings 24 and clamping of such wings between post covers 30 and stent 50 is a more effective way of transferring relatively large forces from leaflets 20 to stent 50 than merely stitching the leaflets to the stent.

Recapitulating and expanding on the foregoing, the clamping forces between sewing ring 40 and stent 50 and/or the clamping forces between post covers 30 and stent 50 are used to secure the leaflets 20 to the stent. The design and manufacturing process (including the various components and the way of assembling those components) greatly reduce possible stress concentration at the stent-leaflet junction by distributing the load more evenly. These design and manufacturing process aspects also (1) reduce the burden of extensive and demanding suturing, (2) increase the consistency of valve manufacturing results, and (3) increase the service life of a resulting valve as a consequence of all of the foregoing factors.

Figure 3:
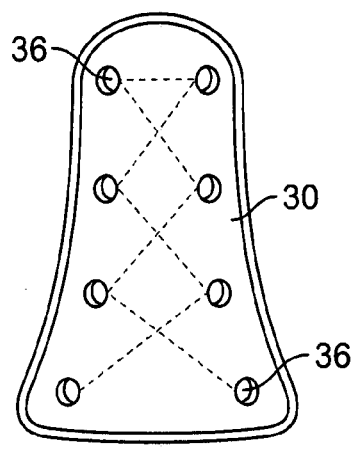
FIG. 3 is a simplified elevational view of one of the components of the valve shown in FIG. 1.
Figure 4:
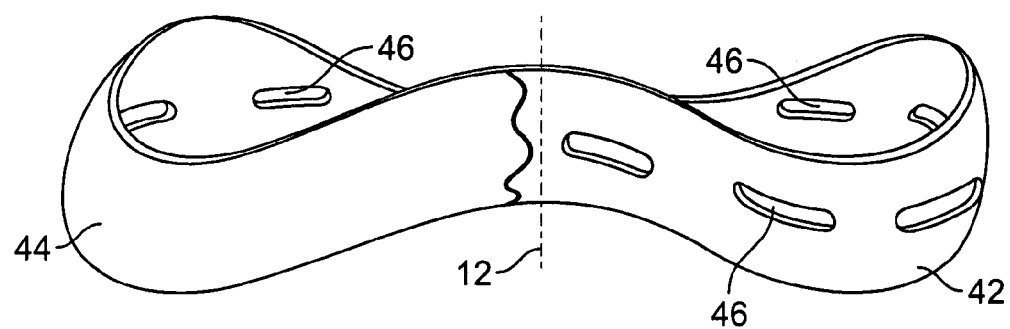
FIG. 4 is a partial view of the same general kind as FIGS. 1 and 2, but showing other components of the valve shown in FIG. 1, and with one of those components partly cut away.
Figure 5:
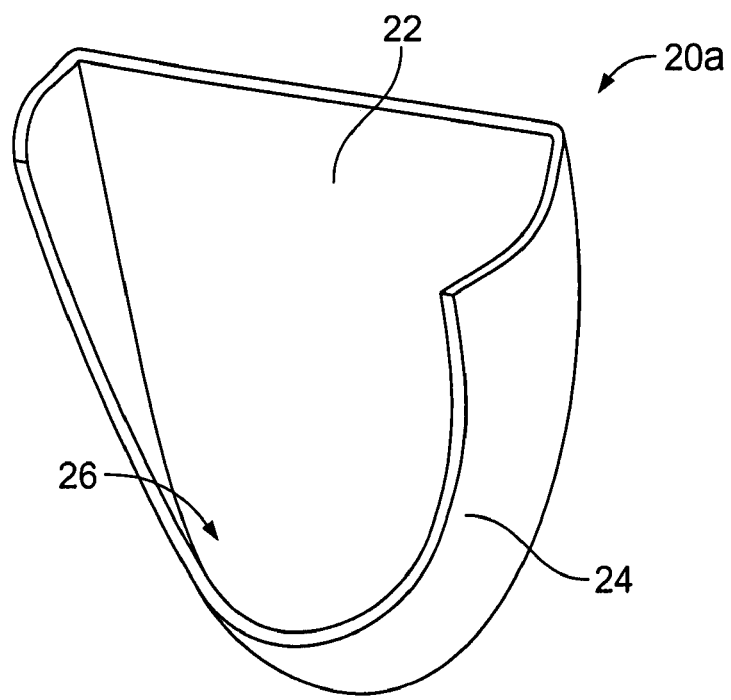
FIG. 5 is a simplified perspective or isometric view of an illustrative embodiment of another component of the valve shown in FIG. 1 in accordance with the invention.

Valve 10 (FIG. 1) may include multiple pre-shaped leaflets 20 (e.g., like representative leaflet 20a on the left in FIG. 2), stent 50 (e.g., as shown exposed on the right in FIG. 2), multiple post covers 30 (e.g., like representative post cover 30 in FIG. 3 and post covers 30*a-c* in FIG. 1), and a sewing cuff 40 (e.g., as in FIG. 1 and FIG. 4 (wherein the right-hand side is broken away to reveal cuff support 42)). The multiple post covers 30 and sewing cuff 40 can, if desired, be integrated into one part without the small gap that is visible in FIG. 1 between the sewing cuff 40 and representative post cover 30*b*.

Figure 6:
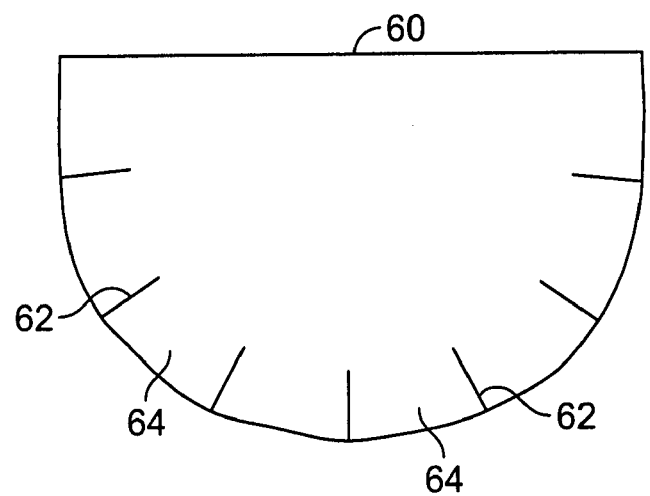
FIG. 6 is a simplified elevational view of an illustrative embodiment of a component of a valve in accordance with the invention at an intermediate stage in the production of that component.
Figure 7:
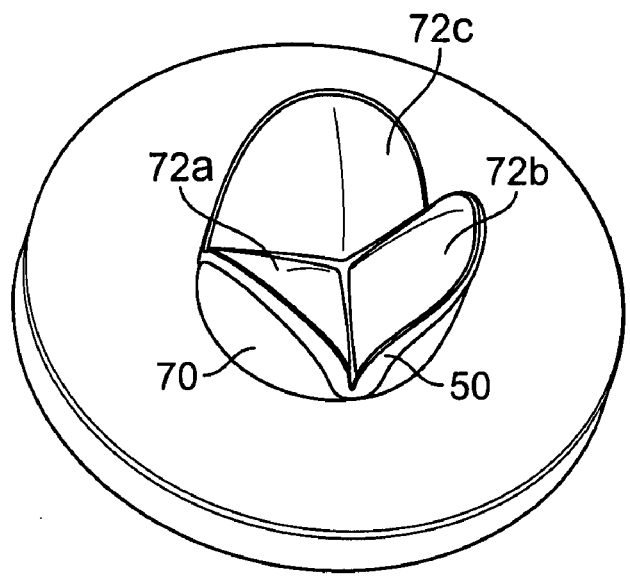
FIG. 7 is a simplified perspective or isometric view of an illustrative component of a valve in accordance with the invention on illustrative tooling that can be used in the production of a valve in accordance with the invention.

The flexible leaflets 20 can be made of polymer, animal or human tissue, tissue engineered materials, or the like. For example, pre-shaped polymer leaflets can be made by starting from a flat sheet of polymer leaflet material that has been cut into a shape like that shown in FIG. 6 for each leaflet. For reference such a leaflet blank will be identified by the number 60. Such blanks 60 can be used in conjunction with a stent 50 that has been placed on a leaflet shaping mold 70 as shown in FIG. 7 and as further described below. As shown in FIG. 7, mold 70 is oriented upside down relative to what is shown in FIG. 1 or FIG. 2. Mold 70 has three regions 72*a-c* that are convex as viewed from above. Each of regions 72 has the shape of the "belly" of a respective one of leaflets 20. The assembly of elements 50 and 70 shown in FIG. 7 is used as follows. Three leaflet blanks like the one shown in FIG. 6 are placed on assembly 50/70 with the straight edges of the blanks meeting in a Y shape at the junctions of belly forms 72*a-c*, and with the curved edge of each blank extending radially out beyond an associated lobe of stent 50. A male forming tool (not shown) is then pushed down onto assembly 50/60/70 to hold the leaflet blanks in place and to cause the leaflet blanks to conform to form bellies 72*a-c*. The radially outward projecting portion of each blank 60 is then folded down over the associated lobe of stent 50. This portion of each blank may be cut radially inwardly from the curved edge as shown at 62 in FIG. 6 to produce a number of separately foldable tabs 64 to facilitate this folding of each leaflet blank edge down around the associated curved lobe of stent 50. Glue may be used to secure the pockets that are thus created along the curved edges of the leaflet blanks. Alternatively or in addition, sewing cuff 40 (or at least cuff support 42) may now be applied around the assembly 50/60/70 to trap at least parts of the folded-down edges of blanks 60 between stent 50 and the applied sewing cuff component. As another possibility, the sewing cuff component may be added to assembled components 50/60 after those components have been removed from mold 70. The male forming tool mentioned earlier (but not shown) can be removed at any convenient time.

Figure 8:
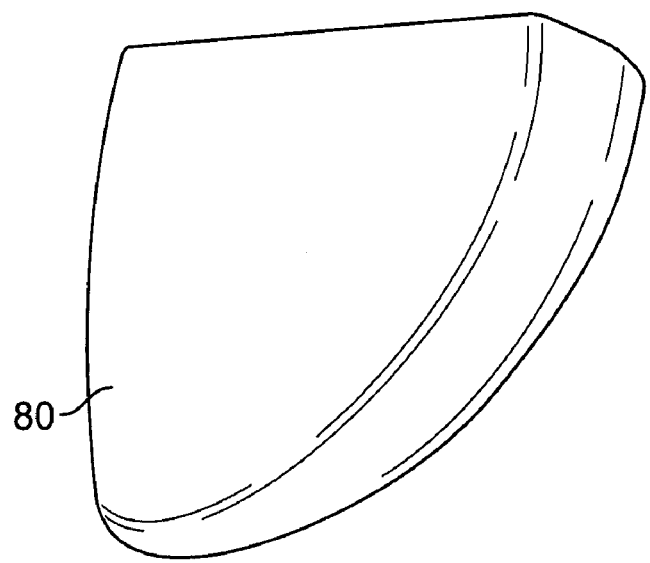
FIG. 8 is a simplified perspective or isometric view of other illustrative tooling that can be used in the production of a valve in accordance with the invention.

Another way that leaflets 20 can be formed (assuming the use of a material for the leaflets that is suitable for formation in this way) is by compress or injunction molding of the leaflets. A mold core 80 like that shown in FIG. 8 can be used in the cavity of such a compress or injection molding machine. Core 80 has the convex shape of a leaflet belly on one side, while the other side is shaped (typically somewhat flatter) to provide the other side 24 of a leaflet pocket 26 (FIG. 5). After a leaflet has been formed around core 80, the leaflet can be removed from the compress or injection molding machine, removed from core 80, and then the "back" or pocket side of the leaflet can be cut away as shown in FIG. 5 to leave only a relatively shallow, curved peripheral edge pocket 26 in which a lobe of stent 50 can be received.

Still another way that leaflets 20 can be formed in the case of tissue leaflets is as follows. A leaflet blank of flat tissue can be provided as shown in FIG. 6. The tissue of the leaflet blank is then shaped around a suitable form (e.g., like core 80 in FIG. 8) by compression. While thus held in the desired shape (i.e., including a leaflet belly shape 22 and a curved edge pocket shape 24/26 folded back behind the belly shape), the tissue is subjected to a fixation process that both stabilizes it for long-term use in a patient and also induces it to retain the shape it had during the fixation process.

In the case of tissue engineered material, the scaffold on which the tissue is grown can be provided with the shape desired for the final leaflet shape. Thus again a core like core 80 in FIG. 8 can be used as the shape around which the scaffold is formed. This gives the scaffold a leaflet belly shape and a curved edge pocket shape folded back behind the belly shape. Tissue grown on a scaffold having this shape results in a tissue engineered leaflet having the same shape (e.g., a shape like that shown in FIG. 5). (The above-mentioned scaffold is typically a biodegradable polymer that provides a matrix for cell growth.)

Chemical bonds and/or adhesives can be used between stent 50 and the rolled back (pocket) portions (e.g., 24, FIG. 5) of the leaflets. However, this may not be necessary in all embodiments. The post covers 30 (which are only radially outward of stent 50) and sewing cuff 40 may be attached to the stent using sutures or other means. The rolled back portions (e.g., 24) of the leaflets are placed between post covers 30 and stent 50, and between sewing ring 40 and stent 50. Sewing ring 40 is assembled at the level of the stent base with both parts having matching and radially aligned apertures and/or slits for attachment. Post covers 30 and stent 50 may also have matching apertures and/or slits for attachment. Because the cuff support 42 of the sewing cuff and post covers 30 are attached to stent 50 by suturing through these matching holes, the suturing work-load is very light and not skill-demanding. (The dotted lines in FIG. 3 show an illustrative suture pattern for attaching a representative post cover 30 to the underlying structure.) Because post covers 30 and sewing ring 40 collectively cover most of the outside surface around the blood inflow edge of the stent, the clamping force between the post covers and the stent and between the sewing ring and the stent is primarily what is responsible for securing the leaflets to the stent. Moreover, this is accomplished with force that is evenly distributed along virtually the entire length of the edge of each leaflet that is adjacent to stent 50. The sutures (or other means) that are used to secure post covers 30 and sewing ring 40 to stent 50 typically pass through the cuff 24 on each leaflet. But the clamping force on these leaflet cuffs 24 between stent 50, on the one hand, and elements 30 and 40, on the other hand, are primarily what secures leaflets 20 to stent 50 and the other elements of the finished valve.

Sewing ring 40 and post covers 30 could be designed as one piece. It is presently preferred, however, to leave a small gap between them (as in the depicted embodiments) to help ensure flexibility of the post regions 52 of the stent in the finished valve. The preferred material of the post covers 30 should be flexible, but yet should provide good clamping force to the portions of the leaflet cuffs 24 that are between the post covers and stent 50. The post cover 30 material can be the same as or different from the material used for sewing cuff support 42 and/or stent 50. Examples of suitable materials for these various components include various biocompatible alloys such as titanium, elgiloy, MP35N, stainless steel, nitinol, etc., and various biocompatible engineering plastics such as acetal polymers, PEEK, etc.

The final gaps between sewing ring 40 and stent 50, between sewing ring 40 and post covers 30, and between post covers 30 and stent 50 can be covered by biocompatible elastomers, such as polyurethane, silicone, and SIBS, or commonly used fabric such as Dacron.

It will be understood that the foregoing is only illustrative of the principles of the invention, and that various modifications can be made by those skilled in the art without departing from the scope and spirit of the invention. For example, the various materials that have been mentioned for various components are only illustrative, and other materials can be used instead if desired.

What is claimed is:

1. A prosthetic heart valve comprising:
    a stent structure that extends annularly around the valve and that includes a plurality of stent post structures that are spaced from one another around the valve;
    a plurality of leaflets that extend radially inward from the stent structure, each of the leaflets being preformed with a pocket that receives at least a portion of the stent structure therein, the pocket having a radially outer portion that lies against a radially outer surface of the stent structure including the stent post structures; and
    a clamping structure that fits over the radially outer portions of the leaflets and that clamps the radially outer portions of the leaflets to the stent structure including the stent post structures substantially along the entire radially outer surface of the stent structure including the stent post structures.

2. The valve defined in claim 1 wherein the radially outer portion of each of the leaflets reaches the radially outer surface of the stent structure by passing around an inflow edge of the stent structure.

3. The valve defined in claim 1 wherein each of the stent post structures comprises two elongated members that extend from a remainder of the stent structure toward a stent post tip that is associated with that stent post structure, the two members of each stent post structure being spaced from one another in a direction that is annular of the valve.

4. The valve defined in claim 3 wherein spacing between the two members of each stent post structure allows parts of the radially outer portions of adjacent ones of the leaflets to pass through that spacing to reach the radially outer surface of those members.

5. The valve defined in claim 1 wherein the stent structure, including the stent post structures, includes a plurality of first apertures that pass radially through the stent structure and that are spaced from one another annularly around the valve, and wherein the clamping structure includes a plurality of second apertures, each of which is radially aligned with a respective one of the first apertures, including those in the stent post structures.

6. The valve defined in claim 5 further comprising:
    securement structure that passes through radially aligned ones of the first and second apertures for securing the clamping structure to the stent structure, including the stent post structures.

7. The valve defined in claim 6 wherein the securement structure also passes through the radially outer portions of the leaflets between the clamping structure and the stent structure, including the stent post structures.

8. The valve defined in claim 6 wherein the securement structure comprises suture material.

9. The valve defined in claim 1 wherein the clamping structure comprises:
    a sewing cuff structure that extends annularly around the valve without covering the stent post structures; and
    a plurality of post covers that are separate from the sewing cuff structure, each of the post covers covering a respective one of the stent post structures.

10. A prosthetic heart valve comprising:
    a stent member that extends annularly around the valve and that includes a plurality of stent post regions substantially parallel to a longitudinal axis that passes through the valve and about which the valve is annular, the stent post regions being spaced from one another in a direction that is annular to the valve;
    a plurality of leaflets that extend radially inward from the stent member, each of the leaflets being preformed with a pocket that receives at least a portion of the stent member therein, the pocket having a radially outer portion that lies against the radially outer surface of the stent member including the stent post regions; and
    a clamping structure that is disposed radially outside of a radially outer surface of the radially outer portions of the leaflets and that clamps the radially outer portions of the leaflets radially inwardly against substantially the entire radially outer surface of the stent member including the stent post regions.

11. The valve defined in claim 10 wherein the radially outer portion of each of the leaflets reaches the radially outer surface of the stent member by passing around an edge of the stent member that is toward a blood-inflow side of the valve when the valve is in use in a patient.

12. The valve defined in claim 10 wherein the clamping structure comprises:
    a sewing cuff structure that extends annularly around the valve without covering the stent post regions; and
    a plurality of post covers that are separate from the sewing cuff structure, each of the post covers covering a respective one of the stent post regions.

13. The valve defined in claim 10 further comprising:
    stitching for securing the clamping structure to the stent member including the stent post regions.

14. The valve defined in claim 13 wherein the stitching passes through preformed and aligned holes in the clamping structure and the stent member including the stent post regions.

15. The valve defined in claim 13 wherein the stitching comprises suture material.

16. The valve defined in claim 1 wherein the clamping structure is stitched to the stent structure including the stent post structures substantially along the entire radially outer surface.

17. The valve defined in claim 10 wherein the clamping structure is stitched to the stent member including the stent post regions substantially along the entire radially outer surface.

18. The valve defined in claim 10 wherein the stent member undulates substantially parallel to the longitudinal axis, the undulations of the stent member causing the stent member to form the plurality of stent post regions, the stent post regions extending from a remainder of the stent member in a blood-outflow direction when the valve is in use in a patient.

* * * * *